(12) United States Patent
Lin

(10) Patent No.: US 11,173,188 B2
(45) Date of Patent: Nov. 16, 2021

(54) ORANGE PEEL FERMENTS AND PREPARATIONS AND APPLICATIONS THEREOF

(71) Applicant: TCI CO., LTD., Taipei (TW)

(72) Inventor: Yung-Hsiang Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 147 days.

(21) Appl. No.: 16/529,264

(22) Filed: Aug. 1, 2019

(65) Prior Publication Data
US 2020/0179476 A1 Jun. 11, 2020

(30) Foreign Application Priority Data
Dec. 6, 2018 (TW) ................................. 107143969

(51) Int. Cl.
| | | |
|---|---|---|
| *A61K 36/752* | (2006.01) | |
| *A61P 25/20* | (2006.01) | |
| *A61P 3/04* | (2006.01) | |
| *A61P 35/00* | (2006.01) | |

(52) U.S. Cl.
CPC .............. *A61K 36/752* (2013.01); *A61P 3/04* (2018.01); *A61P 25/20* (2018.01); *A61P 35/00* (2018.01); *A61K 2236/19* (2013.01)

(58) Field of Classification Search
CPC ..... A61K 36/752; A61K 2236/19; A61P 3/04; A23L 19/07; A23V 2002/00
See application file for complete search history.

(56) References Cited

FOREIGN PATENT DOCUMENTS

| KR | 20100138495 A | * 12/2010 | ............... A23K 1/14 |
|---|---|---|---|

OTHER PUBLICATIONS

Examination report dated Mar. 29, 2021, listed in correspondent China patent application No. 201811621115.7 (publication No. CN 110151848 A).
Use of *Saccharomyces cerevisiae* cells immobilized on orange peel as biocatalyst for alcoholic fermentation. S. Plessas et al., p. 860-865, vol. 98 (2007), Bioresource Technology, May 26, 2006.
Examination report dated Sep. 28, 2021, listed in correspondent China patent application No. 201811621115.7 publication No. CN 110151848 A).
Fermented peel of Citrus sunki Hort. Ex tanaka promotes ethanol metabolism and suppresses body fat accumulation, Zhi-GangCui et al., vol. 16, No. 2, Food Sci. biotechnol, Dec. 31, 2007. Page 311-314, especially last 2 lines in the abstract.
Fermented Extraction of Citrus unshiu Peel Inhibits Viablity and Migration of Human Pancreatic Cancers, Jungwhoi Lee et al., vol. 21, No. 1, Journal of Medicinal Food, Jan. 31, 2018. Page 5-12, especially 4th line to 6th line in the abstract.
Health functions of citrus peel powder processed by press-shear assisted interaction technology, WU Fei Fei et al. vol. 7, No. 8, Journal of Food Safety and Quality, Aug. 31, 2016. Page 3240-3245, especially the last 3-9 lines in the left col. in p. 3244.

* cited by examiner

*Primary Examiner* — Lynn Y Fan
(74) *Attorney, Agent, or Firm* — Chieh-Mei Wang

(57) ABSTRACT

Provided is a method of preparing an orange peel ferment, an orange peel ferment obtained therefrom, and a method for reducing fat accumulation, sleep disturbance, and cancer risk. The orange peel ferment assists obese individuals to slim down via multiple mechanisms including reducing the fat content of adipocytes, promoting lysis of triglycerides in adipocytes, and enhancing the expression of genes involved in fat metabolism, and also reduces sleep disturbance through normalizing circadian rhythm and lowers cancer risk through suppressing expression of cancer risk genes.

9 Claims, 9 Drawing Sheets
Specification includes a Sequence Listing.

ORANGE PEEL FERMENTS AND PREPARATIONS AND APPLICATIONS THEREOF

CROSS-REFERENCE TO RELATED APPLICATION

This application claims priority of Taiwan patent application No. 107143969, filed on Dec. 6, 2018, the content of which is incorporated herein in its entirety by reference.

BACKGROUND OF THE INVENTION

1. Field of the Invention

The present invention relates to a plant ferment and preparations and applications thereof. Particularly, the present invention relates to a method of preparing orange peel ferments, the orange peel ferment obtained by the preparation method, and a method for reducing fat accumulation, sleep disturbance, and cancer risk by using the orange peel ferment.

2. The Prior Art

Most modern people have concerns of obesity due to high-fat and high-sugar diets and insufficient exercise, and therefore have a higher probability of suffering from metabolic diseases such as diabetes, hyperlipidemia, hypertension, cardiovascular diseases, and fatty liver diseases, which are serious threat to individual's health. Scientific studies also show that obesity is an important causing factor of cancers. In addition, obese people are more prone to psychological problems and social disorders. Therefore, a lot of medical research in recent years has focused on seeking approaches to obesity prevention, whereby promoting physical and mental health.

Methods of inhibiting obesity include diet control, exercise, lifestyle changes, medication, and surgery. Surgery is required only by severe obese patients, whereas the general public reduces fat by diet control and exercise. This is because the modern busy-working people have difficulty changing their lifestyles, and they are reluctant to take non-essential medication because of a belief in natural therapies. However, dietary control is difficult to implement because it strictly requires dietary balance and calorie intake; and exercise may cause physical damage if it is not taken appropriately. In addition, these two methods have limited effect on fat loss because they are not directed against fat cells, especially adipose tissue in the viscera.

In view of this, it is of necessity to develop a composition that is convenient for the public to use and effective in reducing fat accumulation, so as to prevent obesity and reduce the possibility of various metabolic diseases and cancers described above.

SUMMARY OF THE INVENTION

Accordingly, in one aspect, the present invention provides a method of preparing an orange peel ferment, including the steps of: (a) preparing a yeast culture including a *Saccharomyces cerevisiae* strain and a carbon source, and (b) adding an orange peel to the yeast culture for fermentation to obtain an orange peel ferment.

In one embodiment of the invention, the weight ratio of the orange peel to the yeast culture is between 1:15 and 3:10.

In one embodiment of the invention, the *Saccharomyces cerevisiae* strain is in an amount ranging from 0.01% to 0.5% by weight of the yeast culture.

In one embodiment of the invention, the carbon source includes a yeast peptone and glucose.

In one embodiment of the invention, the fermentation is performed for 3 to 10 days.

In another aspect, the present invention provides an orange peel ferment obtained by the aforementioned preparation method.

In one further aspect, the present invention provides a method for reducing fat accumulation, sleep disturbance, and cancer risk, including administering to a subject in need a composition including an effective amount of the aforementioned orange peel ferment.

In one embodiment of the invention, the orange peel ferment promotes lysis of triglycerides in an adipocyte.

In one embodiment of the invention, the orange peel ferment enhances expression of a gene encoding low-density lipoprotein (LDL) receptor (LDLR) or adenosine triphosphate (ATP) binding cassette transporter A1 (ABCA1), or combination thereof in an adipocyte.

In one embodiment of the invention, the orange peel ferment enhances expression of a gene encoding silent information regulator 2 homolog 1 (also called sirtuin-1, SIRT1) in a peripheral blood mononuclear cell.

In one embodiment of the invention, the orange peel ferment suppresses expression of a gene encoding lysosomal protein transmembrane 4 alpha (LAPTM4A), G protein-coupled estrogen receptor (GPER), amyloid precursor protein (APP), secretory leucocyte peptidase inhibitor (SLPI), hemoglobin subunit alpha (HBA), Bcl-2-associated X protein (BAX), or suppressor of cytokine signaling 3 (SOCS3), or any combinations thereof.

The present invention discloses that the aforementioned fermentation process yields an orange peel ferment including certain fat-reducing active ingredients that are not present in the orange peel water extract. The orange peel ferment assists obese individuals to slim down via multiple mechanisms including reducing the fat content of adipocytes, promoting lysis of triglycerides in adipocytes, and enhancing the expression of genes involved in fat metabolism, leading to decreased body weight, waist circumference, body mass index (BMI), body fat percentage, and visceral fat index. Given that the waist circumference, visceral fat content, and BMI index are correlated with the incidence of cardiovascular diseases, the disclosed orange peel ferment has the potential to reduce the incidence of cardiovascular diseases. Moreover, administration of an orange peel fermented beverage containing the orange peel ferment can reduce sleep disturbance through normalizing circadian rhythm, and also reduce cancer risk through inhibiting the expression of cancer risk genes. Therefore, the orange peel ferment can be utilized to prepare a composition for reducing fat accumulation, improving sleep quality, and reducing cancer risk. The composition may be in the form of powders, granules, solution, gel or paste and may be manufactured as a pharmaceutical composition, food, a drink, a nutritional supplement, or a reagent that may be administered to a subject orally or via other routes.

The present invention is further explained in the following examples, in reference to the accompanying drawings. It should be understood that the examples given below do not limit the scope of the invention, and that modifications can be made without departing from the scope of the appended claims.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENT

Figure 1:
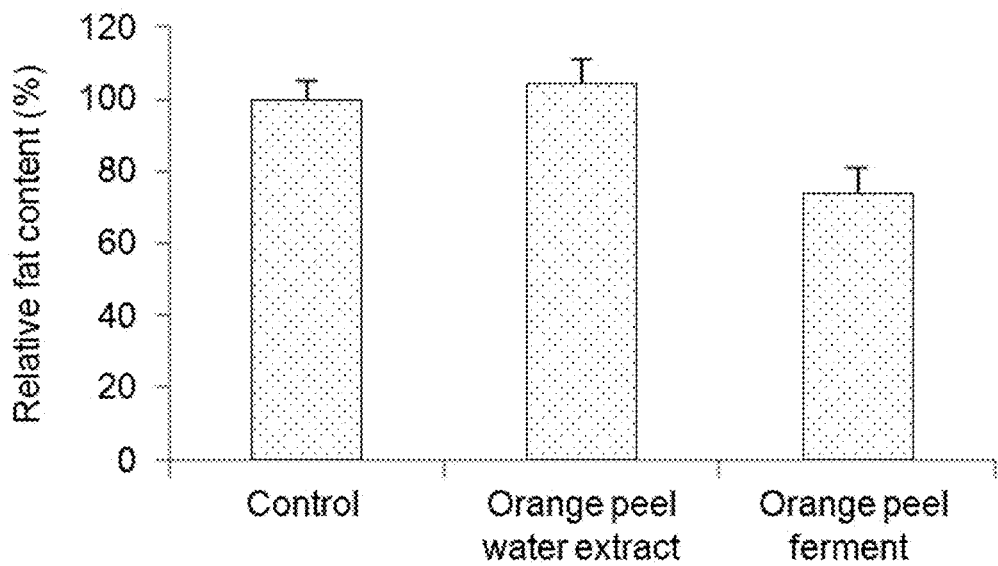
FIG. 1 shows the relative fat content of adipocytes treated with an orange peel ferment according to one embodiment of the present invention or with an orange peel water extract; the relative fat content is relative to the fat content of the control cells.

The present invention provides a method of preparing an orange peel ferment, including the steps of: (a) preparing a yeast culture including a *Saccharomyces cerevisiae* strain and a carbon source, and (b) adding an orange peel to the yeast culture for fermentation to obtain an orange peel ferment. The invention also provides an orange peel ferment obtained by the preparation method. The following examples show that the orange peel ferment can reduce the fat content of adipocytes, promote triglyceride lysis in adipocytes, and enhance the expression of genes involved in fat metabolism. Moreover, administration of an orange peel fermented beverage containing the orange peel ferment helps the obese subject to slim down, and also helps reduce sleep disturbance through normalizing circadian rhythm and lower cancer risk through inhibiting the expression of cancer risk genes.

Definition

Numerical quantities provided herein are approximated, experimental values that may vary within 20 percent, preferably within 10 percent, and most preferably within 5 percent. Thus, the terms "about" and "approximately" refer to within 20 percent, preferably within 10 percent, and most preferably within 5 percent of a given value or range.

The term "an effective amount" as used herein refers to the amount of an active ingredient that is required to confer therapeutic effects on the treated subject.

Materials and Methods

Materials

Minimum Essential Medium α (Gibco MEM-α), fetal bovine serum (Gibco FBS), penicillin/streptomycin (Gibco), and phosphate buffered saline (Gibco PBS), were purchased from Thermo Fisher Scientific. Oil red O was purchased from Sigma. Formaldehyde and isopropanol were purchased from Echo Chemical.

Microorganisms

*Saccharomyces cerevisiae* (BCRC 20271; ATCC 26602) was purchased from the Bioresource Collection and Research Center (BCRC) or the American Type Culture Collection (ATCC).

Cell Culture

Adipocytes used in the following examples were differentiated from mouse stromal cells OP9 (ATCC CRL-2749), which was purchased from ATCC. OP9 cells were seeded at $8 \times 10^4$ cells/well in a 24-well plate, where each well contained 500 μL pre-adipocyte expansion medium (90% MEM-α, 20% FBS, and 1% penicillin/streptomycin), and cultured at 37° C. for 7 days. The medium was refreshed every 3 days during the cell culture with adipocyte differentiation medium (90% MEM-α medium, 20% FBS, and 1% penicillin/streptomycin). After 7 days, complete differentiation into adipocytes were confirmed by examining oil droplets formed in the cells using a microscope (ZEISS; at 400× magnification).

In addition, human peripheral mononuclear cells (PBMC) were isolated from the blood of participants.

Preparations of Oil Red O Staining Solution

The dye, oil red O, was first dissolved thoroughly in 100% isopropanol to prepare a 3 mg/mL oil red O stock solution. To obtain a ready-to-use oil red O staining solution, the stock solution was diluted with double deionized water to a concentration of 1.8 mg/mL and filtered through a 0.22 μm filter immediately before use.

Oil Red O Staining

The neutral fat content of cells was determined by oil red O staining. Prior to staining, the cells were washed with PBS and then fixed with 10% formaldehyde for 30 minutes. The fixed cells were washed once with PBS and rinsed with 60% isopropanol for 1 minute. Thereafter, the cells were stained with the oil red O staining solution for 1 hour and destained with 60% isopropanol for 5 seconds. After staining, the cells were washed with PBS and directly examined by microscope (ZEISS Axio Vert. A1). Alternatively, the intracellular dye was dissolved with 100% isopropanol for 10 minutes and quantified by spectrophotometry. For quantification, 100 μL of the dye-isopropanol solution was transferred to a 96-well plate, and the absorbance at 510 nm was measured using an ELISA (enzyme-linked immunosorbent assay) reader (BioTek). Quantitative results were analyzed for statistical significance based on Student's t-test using the Excel software.

Gene Expression Analysis

The expression levels of genes involved in fat metabolism in cells were measured based on quantitative polymerase chain reaction (qPCR), following the steps briefly described below. According to the manufacturer's instructions, RNA was isolated from cells with RNA Extraction Kit (Geneaid), and 2000 ng of the RNA was reverse transcribed into cDNA at 37° C. using SuperScript® III Reverse Transcriptase (Invitrogen). Thereafter, the cDNA was subjected to qPCR to obtain melting curves. The qPCR was performed with a PCR thermocycler (Step One Plus Real-Time PCR system; Applied Biosystems) using KAPA CYBR FAST qPCR Kit (2×) (KAPA Biosystems) and the primers (shown in TABLE 1) of the target genes and those of the β-actin gene ACTB (as an internal control).

TABLE 1

| Gene | Nucleotide sequences of forward (F) and reverse (R) primers | SEQ ID NO |
|---|---|---|
| ABCA1 | F: AATCATGGTCAATGGAAGGTTCA | 1 |
|  | R: AAGATGGAAGCTGGTATTGTAGCA | 2 |
| SCARB1 | F: ACTCCGACTCTGGGCTCTTCA | 3 |
|  | R: GGCCTCCGGGCTGTAGAA | 4 |
| LDLR | F: TTCACTCCATCTCAAGCATCGA | 5 |
|  | R: GGACAGTAGGTTTTCAGCCAACA | 6 |
| CETP | F: GCCCAGACCAGCAACATTCT | 7 |
|  | R: GATGCCCACAGCGGTGAT | 8 |
| APOA1 | F: CTGTGTACGTGGATGTGCTCAAA | 9 |
|  | R: CAGGCCCTCTGTCTCCTTTTC | 10 |
| ACTB | F: CATGTACGTTGCTATCCAGGC | 11 |
|  | R: CTCCTTAATGTCACGCACGAT | 12 |

Lastly, the $2^{-\Delta\Delta C_T}$ method was used to determine the relative expression of target genes. The cycle threshold ($C_T$) value of the ACTB gene was used as the cycle threshold value of reference gene (internal control). The fold change was calculated according to the following formula:

$\Delta C_T = C_T$ of target gene in experimental or control group $- C_T$ of internal control $\Delta\Delta C_T = \Delta C_T$ of the experimental group $- \Delta C_T$ of the control group Fold change$=2^{-\Delta\Delta Ct\ mean}$.

The expression levels of cancer risk genes in cells were determined according to the aforementioned procedure. TABLE 2 shows the primers of the cancer-risk target genes and those of the 60S acidic ribosomal protein P0 gene RPLP0 (as an internal control).

TABLE 2

| Gene | Nucleotide sequences of forward (F) and reverse (R) primers | SEQ ID NO |
|---|---|---|
| ACP5 | F: CTTCGCAAAGTGCCCTGGTA | 13 |
|  | R: AGTTCCAGCGCTTGGAGATC | 14 |
| S100P | F: AAAGACAAGGATGCCGTGGAT | 15 |
|  | R: TGATTGCAGCCACGAACACT | 16 |
| TKT | F: CAAGCCCCTGGACAGAAAAC | 17 |
|  | R: CTCACCAATGCCACCTTCATAA | 18 |
| DDIT4 | F: GACAGTGCCCTCCAAGACAGA | 19 |
|  | R: GTGGCTGCCTCAGTTTTCCA | 20 |
| LAPTM4A | F: AAACGTGCCGGAGATTGCT | 21 |
|  | R: TGGTTCTTTTTCAGGCATTTTCA | 22 |
| GPER | F: TTCCCCATCGGCTTTGTG | 23 |
|  | R: CCGCCAGGTTGATGAAGTACA | 24 |
| APP | F: GCAGCAGAACGGCTACGAA | 25 |
|  | R: ATGGTTTTGCTGTCCAACTTCA | 26 |
| CD68 | F: CCTCGCCCTGGTGCTTATT | 27 |
|  | R: CACCCCAACCCCCTCAGT | 28 |
| SLP1 | F: ATGGGCATGTGTGGGAAATC | 29 |
|  | R: AAAGGACCTGGACCACACAGA | 30 |
| CTSZ | F: TGTGGAATAATGGCAACAGAAAGA | 31 |
|  | R: CAGCCACAGAAACGACATGGT | 32 |
| CXCR4 | F: CTCCAGTAGCCACCGCATCT | 33 |
|  | R: ATAGTCCCCTGAGCCCATTTC | 34 |
| ADM | F: GTCGGACTCTGGTGTCTTCTAAGC | 35 |
|  | R: TGTACCATGGGCGCCTAAA | 36 |
| HBB | F: CTGGCTCACCTGGACAACCT | 37 |
|  | R: TGCCCAGGAGCCTGAAGTT | 38 |
| HBA | F: CTCCCCGCCGAGTTCAC | 39 |
|  | R: AGGCTCCAGCTTAACGGTATTTG | 40 |
| HP | F: GGGCTCATCAAACTCAAACAGAA | 41 |
|  | R: AACATAACCCACACGCCCTACTT | 42 |
| BAX | F: CCCCCCGAGAGGTCTTTTT | 43 |
|  | R: GGGCCTTGAGCACCAGTTT | 44 |
| FKBP5 | F: GCAGAAAGGGCTTAGTGATGAGAA | 45 |
|  | R: CAGATGCCCCATAAAGACTTGTTAA | 46 |
| SOCS3 | F: GATTCTACTCTGTGCCTCCTGACTATG | 47 |
|  | R: GGCTGAGTATGTGGCTTTCCTATG | 48 |
| RPLP0 | F: TGCATCAGTACCCCATTCTATCA | 49 |
|  | R: GGCCTTGACCTTTTCAGCAA | 50 |

The expression level of sleep-related gene in cells was determined according to the aforementioned procedure. TABLE 3 shows the primers of the sleep-related target gene and those of the glyceraldehyde 3-phosphate dehydrogenase gene GAPDH (as an internal control).

TABLE 3

| Gene | Nucleotide sequences of forward (F) and reverse (R) primers | SEQ ID NO |
|---|---|---|
| SIRT1 | F: TAGCCTTGTCAGATAAGGAAGGA | 51 |
|  | R: ACAGCTTCACAGTCAACTTTGT | 52 |

TABLE 3 -continued

| Gene | Nucleotide sequences of forward (F) and reverse (R) primers | SEQ ID NO |
|---|---|---|
| GAPDH | F: CTGGGCTACACTGAGCACC | 53 |
|  | R: AAGTGGTCGTTGAGGGCAATG | 54 |

For statistical analysis, standard deviation was calculated based on the relative expression of each gene using the STDEV function in the Excel software; and statistical significance of the differences between the data was determined by single-tailed Student's t-test.

Example 1

Preparation of the Orange Peel Ferment

Firstly, mandarin orange (*Citrus reticulata*) peel is washed, dried, and chopped into pieces (about 0.5 to 1 cm in length). Also, a yeast culture medium, that is, an aqueous solution containing 1% to 5% (w/v) yeast peptone and 10% to 15% (w/v) glucose is prepared. The yeast culture medium is optionally heated at 50° C. to 100° C. for 0.5 to 2 hours and then cooled to room temperature. 0.01% to 0.5% (w/v) *Saccharomyces cerevisiae* (BCRC 20271; ATCC 26602) is added to the yeast culture medium and cultured at 25° C. to 35° C. for 3 to 5 days to obtain a yeast culture. Thereafter, the mandarin orange peel and the yeast culture are mixed at a weight ratio of 1:15 to 3:10, and static fermentation is carried out at 25° C. to 35° C. for 3 to 10 days to obtain an orange peel ferment.

The orange peel ferment may be concentrated under reduced pressure at 45° C. to 70° C. to obtain an orange peel ferment concentrate. The orange peel ferment concentrate may further be filtered through a 200 to 400 mesh filter to remove residual solids. The filtered orange peel ferment concentrate is optionally added with 1-3% (w/w) citric acid and 40-70% (w/w) isomalto-oligosaccharide and sterilized to produce an orange peel fermented beverage for drink.

Example 2

The Fat-Reducing Effect of the Orange Peel Ferment

In order to investigate the fat-reducing activity of the orange peel ferment disclosed herein, an orange peel ferment prepared by the method described in Example 1 was assayed for the fat-reducing effect. For comparison, an orange peel water extract without fermentation was prepared by mixing the orange peel with the yeast culture medium described in Example 1 at a weight ratio of 1:5 to 1:15, and carrying out an extraction at 50° C. to 100° C. for 0.5 to 2 hours. During the fat-reducing assay, 0.5% (w/w) of the orange peel ferment (experimental group 1) or 0.5% (w/w) of the orange peel water extract (experimental group 2) was added to a 24-well plate loaded with the adipocytes differentiated from OP9 cells. The adipocytes were cultured at 37° C. for 7 to 10 days, during which the culture medium was refreshed every 3 days with the adipocyte differentiation medium containing 0.5% (w/w) of the orange peel ferment or 0.5% (w/w) of the orange peel water extract. Thereafter, the medium was removed, and the cells of each group were washed with PBS and subjected to oil red O staining for determination of the fat content. The relative fat content is a ratio of the cellular fat content of the experimental group relative to that of the control group (expressed as a percentage). The cells of the control group were treated similarly as mentioned above with the adipocyte differentiation medium alone.

FIG. 1 shows the relative fat content of adipocytes treated with the orange peel ferment or with the orange peel water extract. According to this figure, treatment with the orange peel ferment significantly reduced the fat content of adipocytes compared to the control group, while the orange peel water extract was ineffective. The result indicates that the orange peel fermentation process disclosed herein may yield certain fat-reducing active ingredients that are not present in the orange peel water extract.

Example 3

The Lipolysis Effect of the Orange Peel Ferment

In order to examine the lipolysis effect of the orange peel ferment disclosed herein, adipocytes were treated with the orange peel ferment described in Example 1 and the levels of lipolysis was measured by a lipolysis assay. The assay is carried out by using the glycerol cell-based assay kit (Caymen) which quantifies glycerol that is released from the cells due to intracellular triglyceride hydrolysis. Briefly, 0.25% (w/w) of the orange peel ferment (experimental group) was added to a 24-well plate loaded with the adipocytes differentiated from OP9 cells. The adipocytes were cultured at 37° C. for 7 to 10 days, during which the culture medium was refreshed every 3 days with the adipocyte differentiation medium containing 0.25% (w/w) of the orange peel ferment. Thereafter, the cell culture supernatant was transferred from the 24-well plate to a 96-well plate, and 25 μL/well of the cell culture supernatant was mixed with 100 μL/well of a reagent that detects free glycerol. The resulting mixture was reacted at room temperature for 15 minutes, and then the absorbance at 540 nm was measured using an ELISA dialer (BioTek) to determine the relative glycerol release. The relative glycerol release is a ratio of the glycerol release from cells of the experimental group relative to that of the control group (expressed as a percentage). The cells of the control group were treated similarly as mentioned above with the adipocyte differentiation medium alone.

Figure 2:
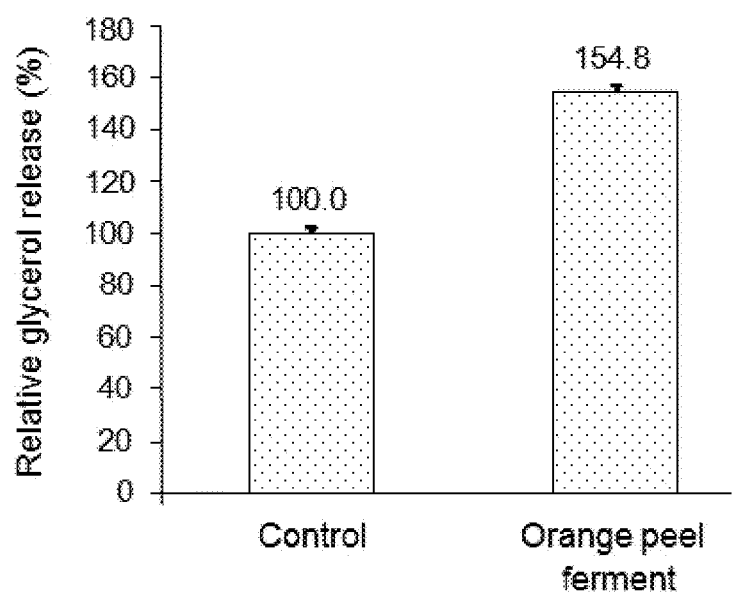
FIG. 2 the relative glycerol release of adipocytes treated with an orange peel ferment according to one embodiment of the present invention; the relative glycerol release is relative to the glycerol release level of the control cells.

FIG. 2 shows the relative glycerol release of adipocytes treated with the orange peel ferment. According to this figure, treatment with the orange peel ferment significantly increased the amount of the released glycerol compared to the control group, indicating that the orange peel ferment can promote the lysis of triglycerides in adipocytes.

Example 4

Enhanced Expression of Genes Involved in Fat Metabolism by the Orange Peel Ferment To investigate the effect of the orange peel ferment on fat metabolism, qPCR was used to determine the expression of fat metabolic genes in the adipocytes differentiated from OP9 cells and treated with the orange peel ferment described in Example 1. The fat metabolic genes include those encoding ATP binding cassette transporter A1 (ABCA1), scavenger receptor class B member 1 (SRB1; encoded by the SCARB1 gene), low-density lipoprotein receptor (LDLR), cholesterol ester transfer protein (CETP), and apolipoprotein A1 (APOA1). Briefly, the cells were seeded at $1 \times 10^5$ cells/well in a 6-well plate, where each well contained 2 mL of the adipocyte differentiation medium. After cell culture at 37° C. for 24 hours, the medium was removed and the cells were washed with PBS. Thereafter, the cells were treated with 1 mL of the adipocyte differentiation medium containing 1 mg/mL orange peel ferment (experimental group 1) or 1 mg/mL of an orange peel water extract as described in Example 2 (experimental group 2), or treated with the adipocyte differentiation medium alone (control group). The three groups of cells were cultured at 37° C. for 48 hours and subjected to qPCR analysis.

Figure 3:
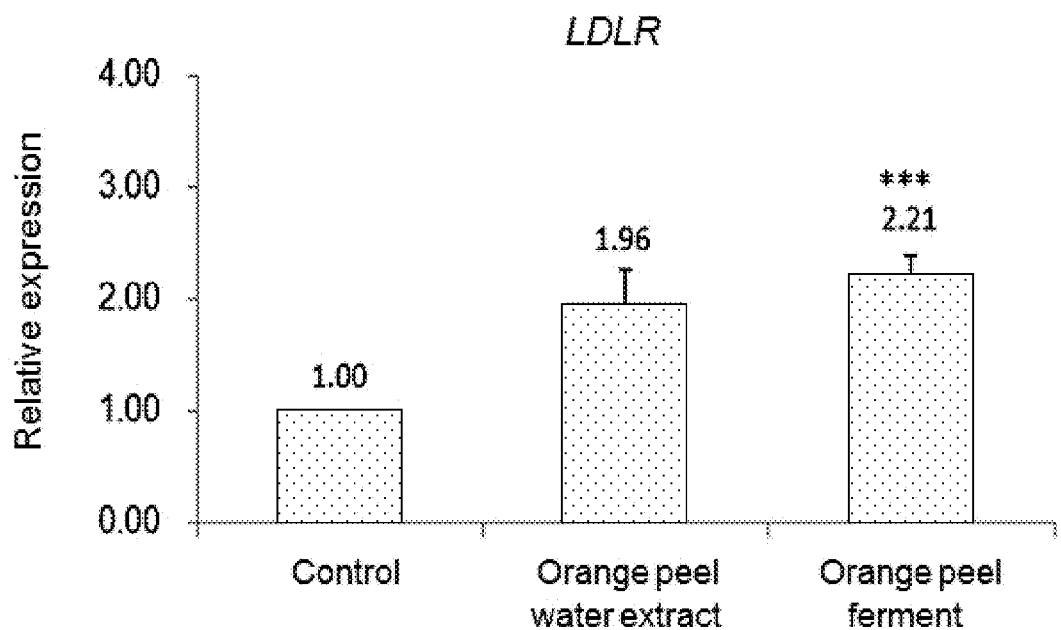
FIG. 3 shows the relative expression of LDLR gene in adipocytes treated with an orange peel ferment according to one embodiment of the present invention or with an orange peel water extract; the relative expression is relative to the expression of the same gene in control cells.
Figure 4:
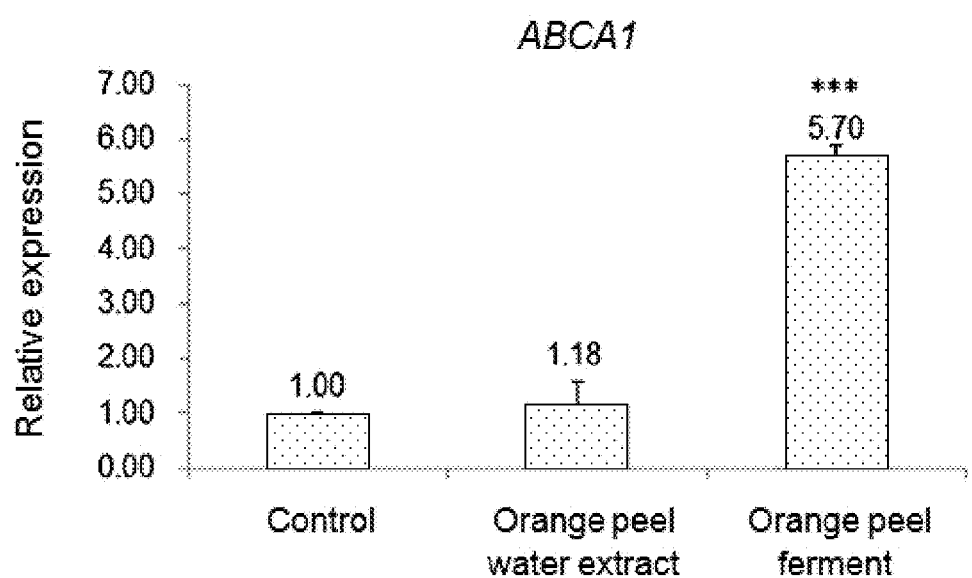
FIG. 4 shows the relative expression of ABCA1 gene of adipocytes treated with an orange peel ferment according to one embodiment of the present invention or with an orange peel water extract; the relative expression is relative to the expression of the same gene in control cells.
Figure 5:
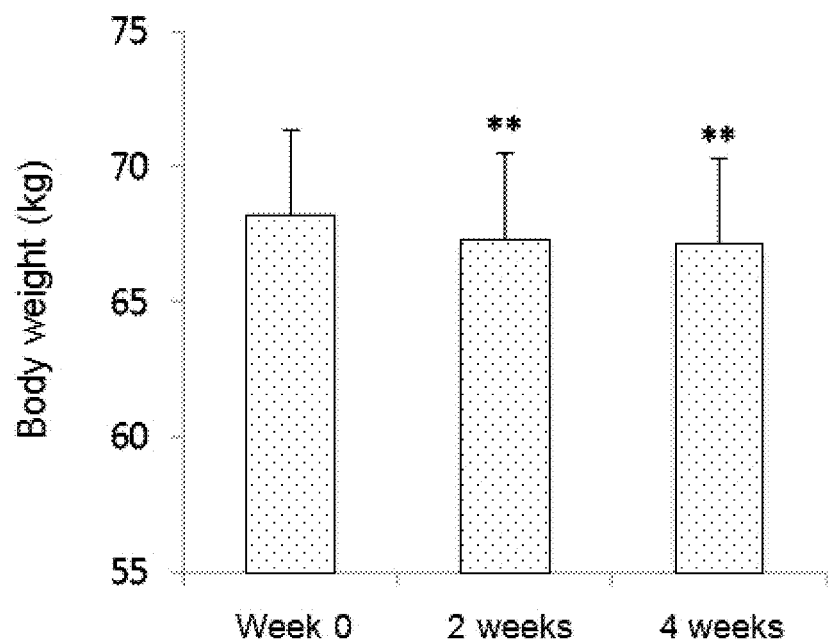
FIG. 5 shows the change in body weight of the subjects administered an orange peel fermented beverage.
Figure 6:
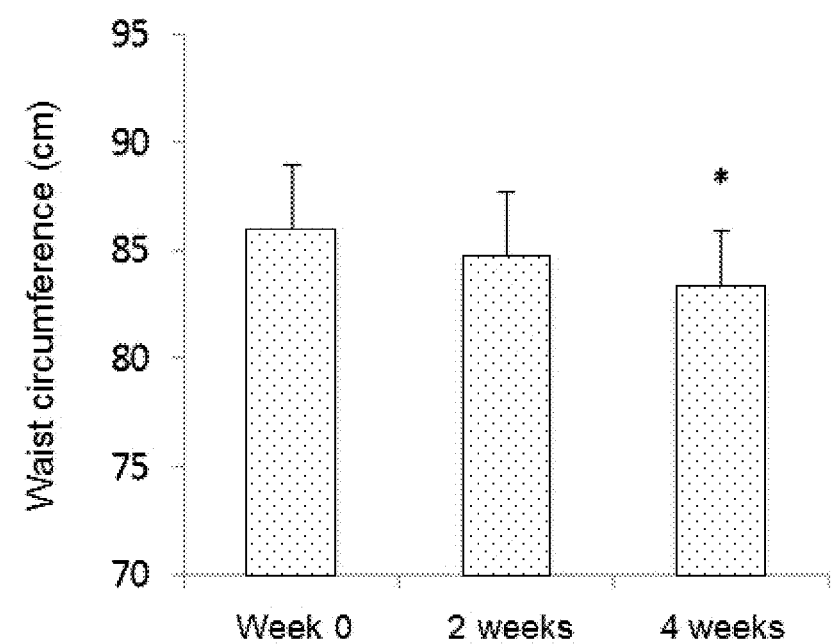
FIG. 6 shows the change in waist circumference of the subjects administered an orange peel fermented beverage.
Figure 7:
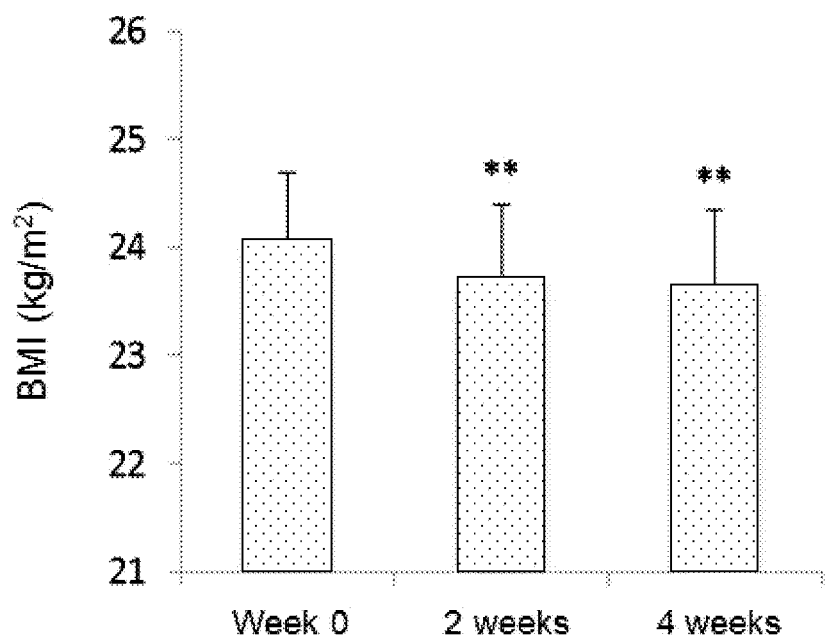
FIG. 7 shows the change in body mass index (BMI) of the subjects administered an orange peel fermented beverage.
Figure 8:
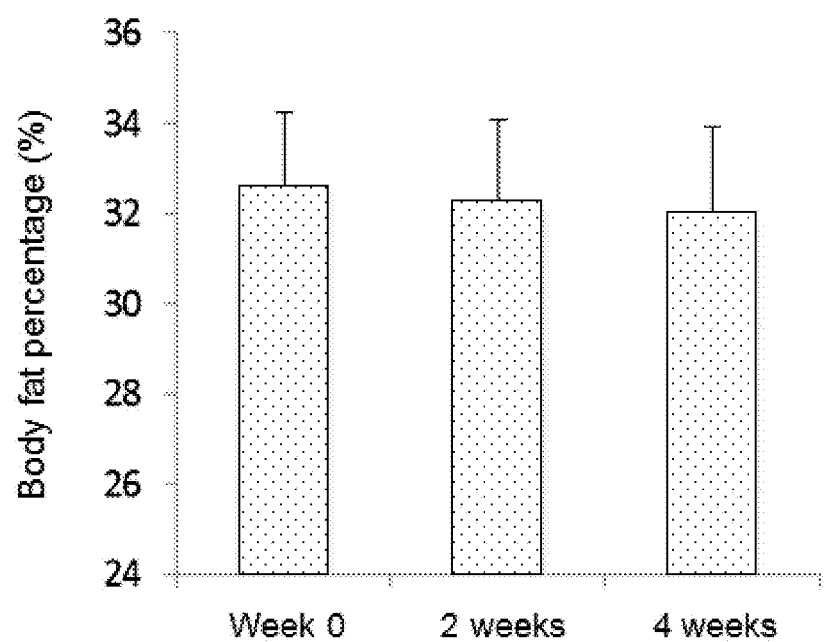
FIG. 8 shows the change in body fat percentage of the subjects administered an orange peel fermented beverage.
Figure 9:
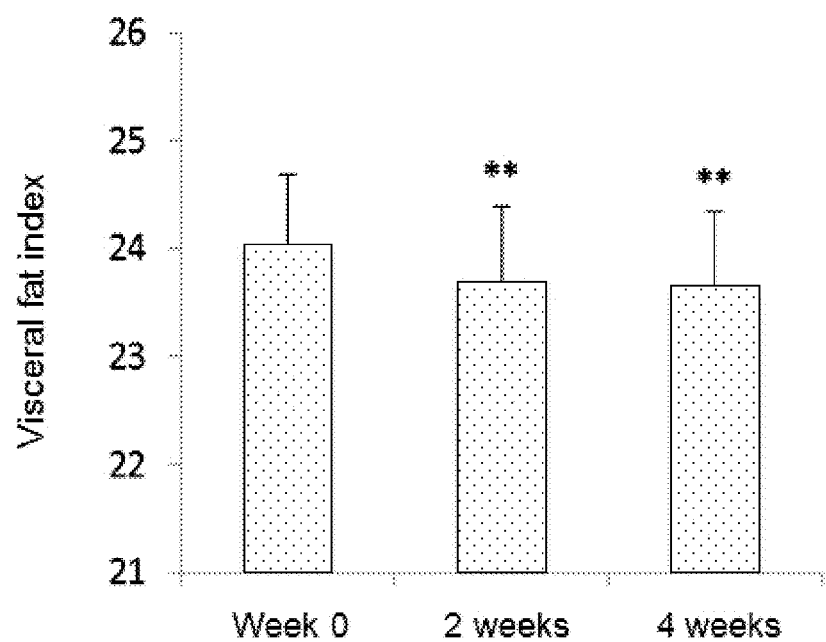
FIG. 9 shows the change in visceral fat index of the subjects administered an orange peel fermented beverage.

FIG. 3 shows the relative expression of LDLR gene in adipocytes treated with the orange peel ferment or with the orange peel water extract; FIG. 4 shows the relative expression of ABCA1 gene of adipocytes treated with the orange peel ferment or with the orange peel water extract; *** in each figure indicates p<0.001 compared to the control group. According to FIGS. 3 and 4, compared to the control group, treatment with the orange peel ferment or the orange peel water extract significantly increased the expression of LDLR gene. Particularly, treatment with the orange peel ferment increased the LDLR gene expression by about 2.2-fold. However, only the treatment with the orange peel ferment significantly increased the expression of ABCA1 gene by about 5.7-fold. The results indicate that the orange peel ferment disclosed herein enhances both the metabolism of low-density lipoprotein cholesterol by hepatocytes and the synthesis of high-density lipoprotein (HDL), thereby contributing to the reduction of cholesterol accumulation in the blood vessel wall and the maintenance of cardiovascular health.

Example 5

The Slimming Effect of the Orange Peel Ferment

In order to examine whether the orange peel ferment disclosed herein possesses a slimming effect, eight obese subjects (with a body fat percentage higher than 27% or a BMI value higher than 24) were daily administered the orange peel fermented beverage (containing 2 g of the orange peel ferment) prepared according to Example 1 for 4 weeks, and the slimming indicators, including body weight, waist circumference, body mass index (BMI), body fat percentage, and visceral fat index, were measured before (week 0) and 2 or 4 weeks after the administration using a body composition monitor (TANITA BC-601FS).

FIGS. 5, 6, 7, 8, and 9 show the changes in the average of body weight, waist circumference, BMI, body fat percentage, and visceral fat index of the subjects administered the orange peel fermented beverage; * indicates p<0.05 and p<0.01, respectively, compared with week 0. According to FIGS. 5 to 9, 4-week administration of the orange peel fermented beverage caused a decrease of about 1.1 kg in body weight, a decrease of about 2.6 cm in waist circumference, a decrease of about 0.4 in BMI, a decrease of about 0.6% in body fat percentage, and a decrease of about 0.5 in visceral fat index, compared to week 0. The results show that long-term use of the orange peel ferment disclosed herein helps obese individuals to slim down.

Example 6

Reduction of Sleep Disturbance by the Orange Peel Ferment

In order to examine the improving effect of the orange peel ferment disclosed herein on sleep disturbance, six subjects with sleep disturbance were daily administered the orange peel fermented beverage (containing 2 g of the orange peel ferment) prepared according to Example 1 for 4 weeks. Peripheral blood mononuclear cells were collected from these subjects before and 4 weeks after the administration for qPCR analysis of the change in the expression of sleep-related genes (such as SIRT1 gene). In addition, the subjects also received a sleep questionnaire to self-evaluate the changes in the degree of sleep disturbance before and after the administration. The degree of sleep disturbance is based on a sleep disturbance score, which is the sum of the scores the subjects get according to the evaluation items listed in TABLE 4 below.

TABLE 4

| | Severity | | | | |
| --- | --- | --- | --- | --- | --- |
| Evaluation items | None | Mild | Moderate | Severe | Very severe |
| Difficulty in falling asleep | 0 | 1 | 2 | 3 | 4 |
| Unable to maintain long sleep | 0 | 1 | 2 | 3 | 4 |
| Wake up early in the morning | 0 | 1 | 2 | 3 | 4 |
| Feeling tired after waking up | 0 | 1 | 2 | 3 | 4 |

Figure 10:
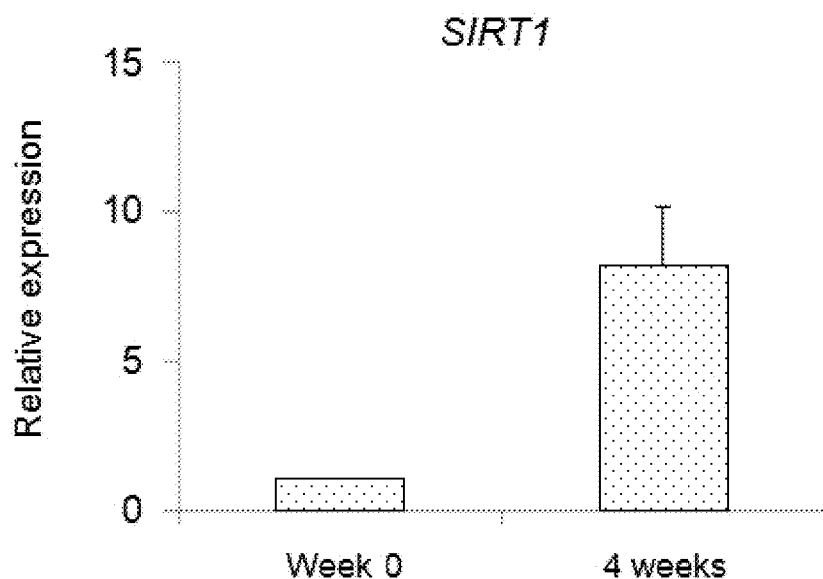
FIG. 10 shows the relative expression of SIRT1 gene in the peripheral blood mononuclear cells of the subjects administered an orange peel fermented beverage for 4 weeks; the relative expression is relative to the expression of the same genes before the administration.

FIG. 10 shows the relative expression of SIRT1 gene in peripheral blood mononuclear cells of the subjects after administered the orange peel fermented beverage. According to this figure, compared with week 0, 4-week administration of the orange peel fermented beverage increased the expression of SIRT1 gene by about 8-fold. In view of previous studies showing that the SIRT1 protein regulates the expression of circadian genes and establishes circadian rhythm, and that the SIRT1 expression decreases with aging, these data indicate that long-term use of the orange peel ferment disclosed herein is beneficial to normal circadian rhythmicity, and even assists the elderly maintain a normal circadian clock.

Figure 11:
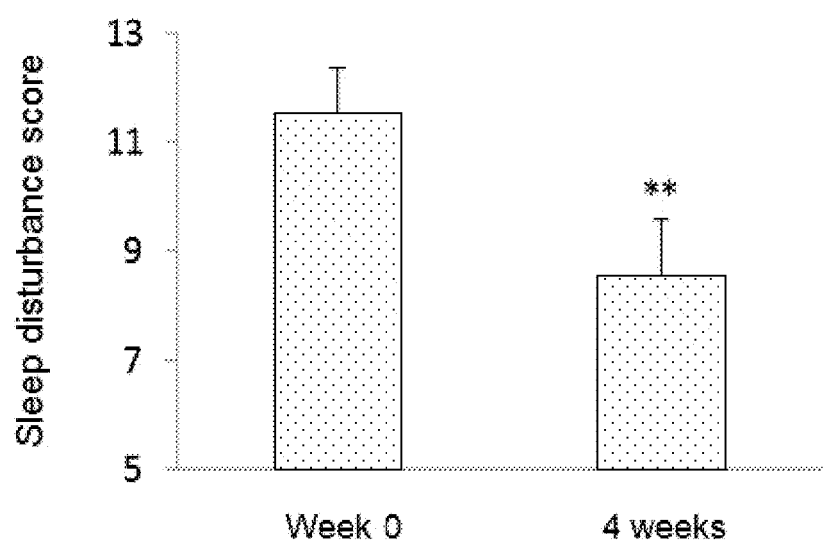
FIG. 11 shows the sleep disturbance score for the subjects administered an orange peel fermented beverage for 4 weeks.
Figure 12A:
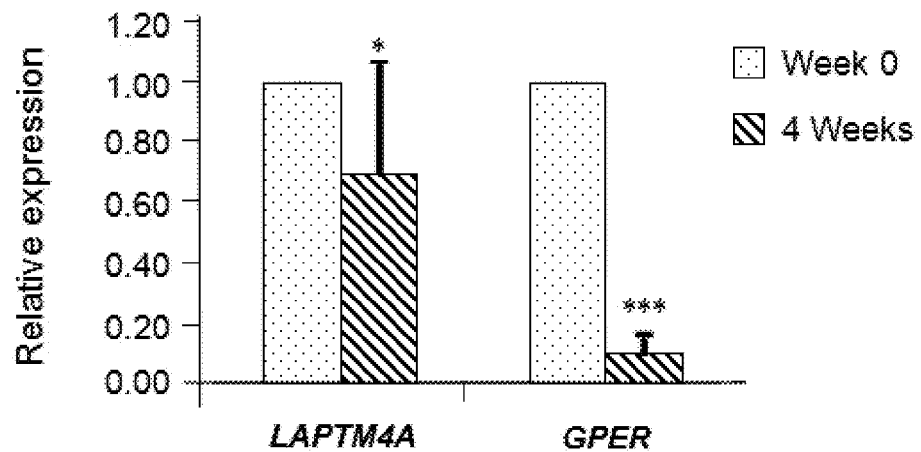
FIG. 12A shows the relative expression of LAPTM4A and GPER genes in the peripheral blood mononuclear cells of the subjects administered an orange peel fermented beverage for 4 weeks; the relative expression is relative to the expression of the same genes before the administration.
Figure 12B:
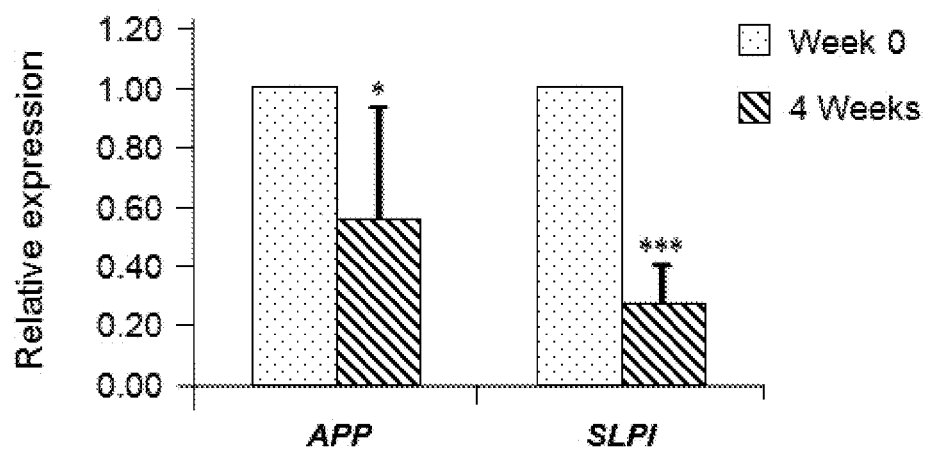
FIG. 12B shows the relative expression of APP and SLPI genes in the peripheral blood mononuclear cells of the subjects administered an orange peel fermented beverage for 4 weeks; the relative expression is relative to the expression of the same genes before the administration.
Figure 12C:
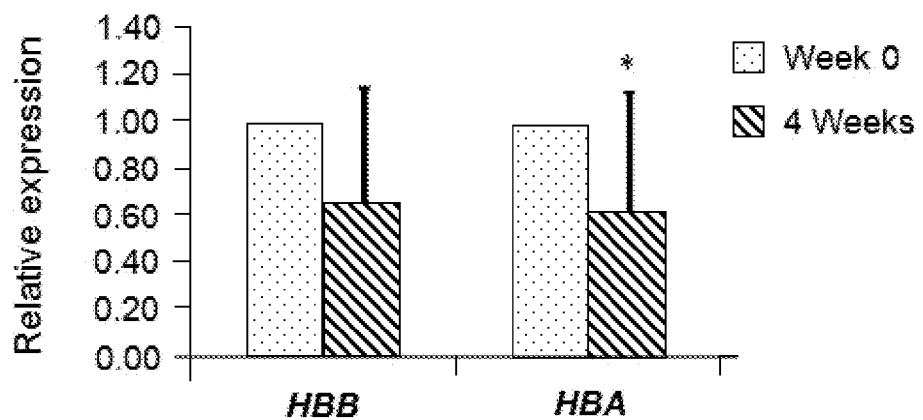
FIG. 12C shows the relative expression of HBB and HBA genes in the peripheral blood mononuclear cells of the subjects administered an orange peel fermented beverage for 4 weeks; the relative expression is relative to the expression of the same genes before the administration.
Figure 12D:
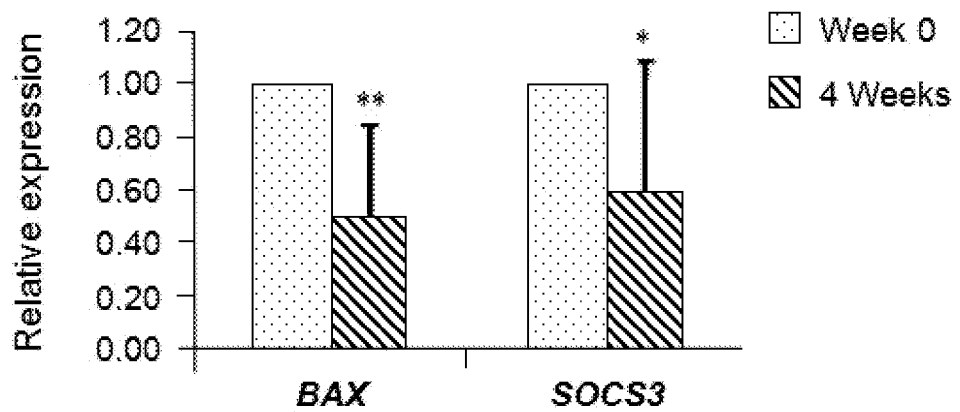
FIG. 12D shows the relative expression of BAX and SOCS3 genes in the peripheral blood mononuclear cells of the subjects administered an orange peel fermented beverage for 4 weeks; the relative expression is relative to the expression of the same genes before the administration.

FIG. 11 shows the change in the average of sleep disturbance scores for the subjects administered the orange peel fermented beverage. According to this figure, compared with week 0, 4-week administration of the orange peel fermented beverage significantly reduced sleep disturbance of the subjects by about 26%. The result indicates that long-term use of the orange peel ferment disclosed herein can improve sleep quality.

Example 7

Reduction of Cancer Risk by the Orange Peel Ferment

In order to examine whether the orange peel ferment disclosed herein reduces cancer risks, six subjects were daily administered the orange peel fermented beverage (containing 2 g of the orange peel ferment) prepared according to Example 1 for 4 weeks. Peripheral blood mononuclear cells were collected from these subjects before and 4 weeks after the administration for qPCR analysis of the change in the expression of cancer risk genes. The so-called cancer risk genes are divided into four groups, including (1) genes that promote cell growth and enable cells to escape apoptosis, including the lysosomal protein transmembrane 4 alpha (LAPTM4A) gene and the G-protein coupled estrogen receptor (GPER) gene; (2) genes that involved in cell migration and invasion, including the amyloid precursor protein (APP) gene and the secretory leukocyte peptidase inhibitor (SLPI) gene; (3) genes that involved in circulation and nutrient supply, including the hemoglobin subunit beta (HBB) and hemoglobin subunit alpha (HBA) genes; and (4) genes that enable cells to escape immune killing, including the Bcl-2-associated X protein (BAX) gene and the suppressor of cytokine signaling 3 (SOCS3) gene.

FIGS. 12A to 12D show the relative expression of cancer risk genes in the peripheral blood mononuclear cells of the subjects after administered the orange peel fermented beverage; *, , and * indicates $p<0.05$, $p<0.01$, and $p<0.001$, respectively, compared to the gene expression before the administration. According to FIGS. 12A to 12D, compared with week 0, 4-week administration of the orange peel fermented beverage generally suppressed the expression of the aforementioned four groups of cancer risk genes, especially the LAPTM4A, GPER, APP, SLPI, HBA, BAX, and SOCS3 genes.

Figure 13:
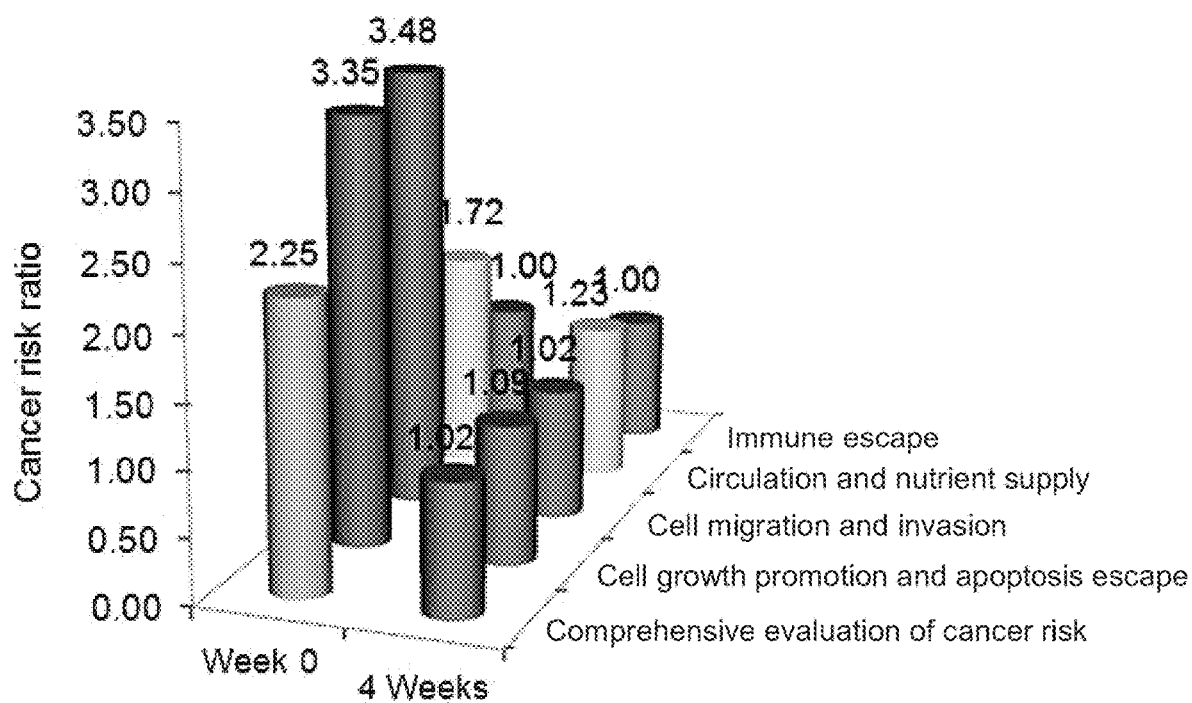
FIG. 13 shows the cancer risk ratio for the subjects administered an orange peel fermented beverage for 4 weeks.

The cancer risk ratios for the subjects before and after taking the orange peel fermented beverage were estimated, by comparing the relative expression of the aforementioned cancer risk genes with the data in TCI Gene Database (constructed based on the genomic data of sub-healthy individuals), and shown in the FIG. 13. According to this figure, 4-week administration of the orange peel fermented beverage reduced the cancer risk ratio, indicating decreased cancer occurrence. The results show that long-term use of the orange peel ferment disclosed herein can reduce cancer risk.

In conclusion, the data presented above show that the orange peel fermentation process disclosed herein yields an orange peel ferment including certain fat-reducing active ingredients that are not present in the orange peel water extract. The orange peel ferment assists obese individuals to slim down via multiple mechanisms including reducing the fat content of adipocytes, promoting lysis of triglycerides in adipocytes, and enhancing the expression of genes involved in fat metabolism. Moreover, administration of an orange peel fermented beverage containing the orange peel ferment can reduce sleep disturbance through normalizing circadian rhythm, and also lower cancer risk through inhibiting the expression of cancer risk genes. Therefore, the orange peel ferment can be utilized to prepare a composition for reducing fat accumulation, improving sleep quality, and reducing cancer risk. The composition may be in the form of powders, granules, solution, gel or paste and may be manufactured as a pharmaceutical composition, food, a drink, a nutritional supplement, or a reagent that may be administered to a subject orally or via other routes.

The present invention has been described with reference to the above preferred embodiments. However, it will be apparent to those skilled in the art that modifications and changes in form and detail may be made without departing from the scope of the present invention defined by the appended claims.

What is claimed is:

1. A method for reducing fat accumulation, sleep disturbance, and cancer risk, comprising administering to a human in need thereof a composition comprising 2 g/day of an orange peel ferment, wherein the orange peel ferment is obtained by the steps of:
   (a) preparing a yeast culture comprising a *Saccharomyces cerevisiae* strain and a carbon source, wherein the carbon source comprises a yeast peptone and glucose; and
   (b) adding an orange peel to the yeast culture for fermentation to obtain the orange peel ferment.

2. The method of claim 1, wherein the orange peel ferment promotes lysis of triglycerides in an adipocyte.

3. The method of claim 1, wherein the orange peel ferment enhances expression of a gene encoding low-density lipoprotein (LDL) receptor (LDLR) or adenosine triphosphate binding cassette transporter A1 (ABCA1), or combination thereof in an adipocyte.

4. The method of claim 1, wherein the orange peel ferment enhances expression of a gene encoding silent information regulator 2 homolog 1 (SIRT1).

5. The method of claim 1, wherein the orange peel ferment suppresses expression of a gene encoding lysosomal protein transmembrane 4 alpha (LAPTM4A), G protein-coupled estrogen receptor (GPER), amyloid precursor protein (APP), secretory leucocyte peptidase inhibitor (SLPI), hemoglobin subunit alpha (HBA), Bcl-2-associated X protein (BAX), suppressor of cytokine signaling 3 (SOCS3), or any combinations thereof.

6. The method of claim 1, wherein the composition is administered for 4 weeks.

7. The method of claim 1, wherein the weight ratio of the orange peel to the yeast culture is between 1:15 and 3:10.

8. The method of claim 1, wherein the *Saccharomyces cerevisiae* strain is in an amount ranging from 0.01% to 0.5% by weight of the yeast culture.

9. The method of claim 1, wherein the fermentation is performed for 3 to 10 days.

* * * * *

SEQUENCE LISTING

```
<160> NUMBER OF SEQ ID NOS: 54

<210> SEQ ID NO 1
<211> LENGTH: 23
<212> TYPE: DNA
<213> ORGANISM: Artificial sequence
<220> FEATURE:
<223> OTHER INFORMATION: PCR primer

<400> SEQUENCE: 1
aatcatggtc aatggaaggt tca                                           23

<210> SEQ ID NO 2
<211> LENGTH: 24
<212> TYPE: DNA
<213> ORGANISM: Artificial sequence
<220> FEATURE:
<223> OTHER INFORMATION: PCR primer

<400> SEQUENCE: 2
aagatggaag ctggtattgt agca                                          24

<210> SEQ ID NO 3
<211> LENGTH: 21
<212> TYPE: DNA
<213> ORGANISM: Artificial sequence
<220> FEATURE:
<223> OTHER INFORMATION: PCR primer

<400> SEQUENCE: 3
actccgactc tgggctcttc a                                             21

<210> SEQ ID NO 4
<211> LENGTH: 18
<212> TYPE: DNA
<213> ORGANISM: Artificial sequence
<220> FEATURE:
<223> OTHER INFORMATION: PCR primer
```

<400> SEQUENCE: 4
ggcctccggg ctgtagaa                                          18

<210> SEQ ID NO 5
<211> LENGTH: 22
<212> TYPE: DNA
<213> ORGANISM: Artificial sequence
<220> FEATURE:
<223> OTHER INFORMATION: PCR primer

<400> SEQUENCE: 5
ttcactccat ctcaagcatc ga                                     22

<210> SEQ ID NO 6
<211> LENGTH: 23
<212> TYPE: DNA
<213> ORGANISM: Artificial sequence
<220> FEATURE:
<223> OTHER INFORMATION: PCR primer

<400> SEQUENCE: 6
ggacagtagg ttttcagcca aca                                    23

<210> SEQ ID NO 7
<211> LENGTH: 20
<212> TYPE: DNA
<213> ORGANISM: Artificial sequence
<220> FEATURE:
<223> OTHER INFORMATION: PCR primer

<400> SEQUENCE: 7
gcccagacca gcaacattct                                        20

<210> SEQ ID NO 8
<211> LENGTH: 18
<212> TYPE: DNA
<213> ORGANISM: Artificial sequence
<220> FEATURE:
<223> OTHER INFORMATION: PCR primer

<400> SEQUENCE: 8
gatgcccaca gcggtgat                                          18

<210> SEQ ID NO 9
<211> LENGTH: 23
<212> TYPE: DNA
<213> ORGANISM: Artificial sequence
<220> FEATURE:
<223> OTHER INFORMATION: PCR primer

<400> SEQUENCE: 9
ctgtgtacgt ggatgtgctc aaa                                    23

<210> SEQ ID NO 10
<211> LENGTH: 21
<212> TYPE: DNA
<213> ORGANISM: Artificial sequence
<220> FEATURE:
<223> OTHER INFORMATION: PCR primer

<400> SEQUENCE: 10
caggccctct gtctcctttt c                                      21

<210> SEQ ID NO 11
<211> LENGTH: 21

```
<212> TYPE: DNA
<213> ORGANISM: Artificial sequence
<220> FEATURE:
<223> OTHER INFORMATION: PCR primer

<400> SEQUENCE: 11
catgtacgtt gctatccagg c                                              21

<210> SEQ ID NO 12
<211> LENGTH: 21
<212> TYPE: DNA
<213> ORGANISM: Artificial sequence
<220> FEATURE:
<223> OTHER INFORMATION: PCR primer

<400> SEQUENCE: 12
ctccttaatg tcacgcacga t                                              21

<210> SEQ ID NO 13
<211> LENGTH: 20
<212> TYPE: DNA
<213> ORGANISM: Artificial sequence
<220> FEATURE:
<223> OTHER INFORMATION: PCR primer

<400> SEQUENCE: 13
cttcgcaaag tgccctggta                                                20

<210> SEQ ID NO 14
<211> LENGTH: 20
<212> TYPE: DNA
<213> ORGANISM: Artificial sequence
<220> FEATURE:
<223> OTHER INFORMATION: PCR primer

<400> SEQUENCE: 14
agttccagcg cttggagatc                                                20

<210> SEQ ID NO 15
<211> LENGTH: 21
<212> TYPE: DNA
<213> ORGANISM: Artificial sequence
<220> FEATURE:
<223> OTHER INFORMATION: PCR primer

<400> SEQUENCE: 15
aaagacaagg atgccgtgga t                                              21

<210> SEQ ID NO 16
<211> LENGTH: 20
<212> TYPE: DNA
<213> ORGANISM: Artificial sequence
<220> FEATURE:
<223> OTHER INFORMATION: PCR primer

<400> SEQUENCE: 16
tgattgcagc cacgaacact                                                20

<210> SEQ ID NO 17
<211> LENGTH: 20
<212> TYPE: DNA
<213> ORGANISM: Artificial sequence
<220> FEATURE:
<223> OTHER INFORMATION: PCR primer

<400> SEQUENCE: 17
```
caagcccctg gacagaaaac                                                20

<210> SEQ ID NO 18
<211> LENGTH: 22
<212> TYPE: DNA
<213> ORGANISM: Artificial sequence
<220> FEATURE:
<223> OTHER INFORMATION: PCR primer

<400> SEQUENCE: 18
ctcaccaatg ccaccttcat aa                                             22

<210> SEQ ID NO 19
<211> LENGTH: 21
<212> TYPE: DNA
<213> ORGANISM: Artificial sequence
<220> FEATURE:
<223> OTHER INFORMATION: PCR primer

<400> SEQUENCE: 19
gacagtgccc tccaagacag a                                              21

<210> SEQ ID NO 20
<211> LENGTH: 20
<212> TYPE: DNA
<213> ORGANISM: Artificial sequence
<220> FEATURE:
<223> OTHER INFORMATION: PCR primer

<400> SEQUENCE: 20
gtggctgcct cagttttcca                                                20

<210> SEQ ID NO 21
<211> LENGTH: 19
<212> TYPE: DNA
<213> ORGANISM: Artificial sequence
<220> FEATURE:
<223> OTHER INFORMATION: PCR primer

<400> SEQUENCE: 21
aaacgtgccg gagattgct                                                 19

<210> SEQ ID NO 22
<211> LENGTH: 23
<212> TYPE: DNA
<213> ORGANISM: Artificial sequence
<220> FEATURE:
<223> OTHER INFORMATION: PCR primer

<400> SEQUENCE: 22
tggttctttt tcaggcattt tca                                            23

<210> SEQ ID NO 23
<211> LENGTH: 18
<212> TYPE: DNA
<213> ORGANISM: Artificial sequence
<220> FEATURE:
<223> OTHER INFORMATION: PCR primer

<400> SEQUENCE: 23
ttccccatcg gctttgtg                                                  18

<210> SEQ ID NO 24
<211> LENGTH: 21
<212> TYPE: DNA
<213> ORGANISM: Artificial sequence

```
<220> FEATURE:
<223> OTHER INFORMATION: PCR primer

<400> SEQUENCE: 24
ccgccaggtt gatgaagtac a                                          21

<210> SEQ ID NO 25
<211> LENGTH: 19
<212> TYPE: DNA
<213> ORGANISM: Artificial sequence
<220> FEATURE:
<223> OTHER INFORMATION: PCR primer

<400> SEQUENCE: 25
gcagcagaac ggctacgaa                                             19

<210> SEQ ID NO 26
<211> LENGTH: 22
<212> TYPE: DNA
<213> ORGANISM: Artificial sequence
<220> FEATURE:
<223> OTHER INFORMATION: PCR primer

<400> SEQUENCE: 26
atggttttgc tgtccaactt ca                                         22

<210> SEQ ID NO 27
<211> LENGTH: 19
<212> TYPE: DNA
<213> ORGANISM: Artificial sequence
<220> FEATURE:
<223> OTHER INFORMATION: PCR primer

<400> SEQUENCE: 27
cctcgccctg gtgcttatt                                             19

<210> SEQ ID NO 28
<211> LENGTH: 18
<212> TYPE: DNA
<213> ORGANISM: Artificial sequence
<220> FEATURE:
<223> OTHER INFORMATION: PCR primer

<400> SEQUENCE: 28
caccccaacc ccctcagt                                              18

<210> SEQ ID NO 29
<211> LENGTH: 20
<212> TYPE: DNA
<213> ORGANISM: Artificial sequence
<220> FEATURE:
<223> OTHER INFORMATION: PCR primer

<400> SEQUENCE: 29
atgggcatgt gtgggaaatc                                            20

<210> SEQ ID NO 30
<211> LENGTH: 21
<212> TYPE: DNA
<213> ORGANISM: Artificial sequence
<220> FEATURE:
<223> OTHER INFORMATION: PCR primer

<400> SEQUENCE: 30
aaaggacctg gaccacacag a                                          21
```

```
<210> SEQ ID NO 31
<211> LENGTH: 24
<212> TYPE: DNA
<213> ORGANISM: Artificial sequence
<220> FEATURE:
<223> OTHER INFORMATION: PCR primer

<400> SEQUENCE: 31
tgtggaataa tggcaacaga aaga                                          24

<210> SEQ ID NO 32
<211> LENGTH: 21
<212> TYPE: DNA
<213> ORGANISM: Artificial sequence
<220> FEATURE:
<223> OTHER INFORMATION: PCR primer

<400> SEQUENCE: 32
cagccacaga aacgacatgg t                                             21

<210> SEQ ID NO 33
<211> LENGTH: 20
<212> TYPE: DNA
<213> ORGANISM: Artificial sequence
<220> FEATURE:
<223> OTHER INFORMATION: PCR primer

<400> SEQUENCE: 33
ctccagtagc caccgcatct                                               20

<210> SEQ ID NO 34
<211> LENGTH: 21
<212> TYPE: DNA
<213> ORGANISM: Artificial sequence
<220> FEATURE:
<223> OTHER INFORMATION: PCR primer

<400> SEQUENCE: 34
atagtcccct gagcccattt c                                             21

<210> SEQ ID NO 35
<211> LENGTH: 24
<212> TYPE: DNA
<213> ORGANISM: Artificial sequence
<220> FEATURE:
<223> OTHER INFORMATION: PCR primer

<400> SEQUENCE: 35
gtcggactct ggtgtcttct aagc                                          24

<210> SEQ ID NO 36
<211> LENGTH: 19
<212> TYPE: DNA
<213> ORGANISM: Artificial sequence
<220> FEATURE:
<223> OTHER INFORMATION: PCR primer

<400> SEQUENCE: 36
tgtaccatgg gcgcctaaa                                                19

<210> SEQ ID NO 37
<211> LENGTH: 20
<212> TYPE: DNA
<213> ORGANISM: Artificial sequence
<220> FEATURE:
<223> OTHER INFORMATION: PCR primer
```

<400> SEQUENCE: 37
ctggctcacc tggacaacct                                                    20

<210> SEQ ID NO 38
<211> LENGTH: 19
<212> TYPE: DNA
<213> ORGANISM: Artificial sequence
<220> FEATURE:
<223> OTHER INFORMATION: PCR primer

<400> SEQUENCE: 38
tgcccaggag cctgaagtt                                                     19

<210> SEQ ID NO 39
<211> LENGTH: 17
<212> TYPE: DNA
<213> ORGANISM: Artificial sequence
<220> FEATURE:
<223> OTHER INFORMATION: PCR primer

<400> SEQUENCE: 39
ctccccgccg agttcac                                                       17

<210> SEQ ID NO 40
<211> LENGTH: 23
<212> TYPE: DNA
<213> ORGANISM: Artificial sequence
<220> FEATURE:
<223> OTHER INFORMATION: PCR primer

<400> SEQUENCE: 40
aggctccagc ttaacggtat ttg                                                23

<210> SEQ ID NO 41
<211> LENGTH: 23
<212> TYPE: DNA
<213> ORGANISM: Artificial sequence
<220> FEATURE:
<223> OTHER INFORMATION: PCR primer

<400> SEQUENCE: 41
gggctcatca aactcaaaca gaa                                                23

<210> SEQ ID NO 42
<211> LENGTH: 23
<212> TYPE: DNA
<213> ORGANISM: Artificial sequence
<220> FEATURE:
<223> OTHER INFORMATION: PCR primer

<400> SEQUENCE: 42
aacataaccc acacgcccta ctt                                                23

<210> SEQ ID NO 43
<211> LENGTH: 19
<212> TYPE: DNA
<213> ORGANISM: Artificial sequence
<220> FEATURE:
<223> OTHER INFORMATION: PCR primer

<400> SEQUENCE: 43
ccccccgaga ggtcttttt                                                     19

<210> SEQ ID NO 44

<211> LENGTH: 19
<212> TYPE: DNA
<213> ORGANISM: Artificial sequence
<220> FEATURE:
<223> OTHER INFORMATION: PCR primer

<400> SEQUENCE: 44
gggccttgag caccagttt                                            19

<210> SEQ ID NO 45
<211> LENGTH: 24
<212> TYPE: DNA
<213> ORGANISM: Artificial sequence
<220> FEATURE:
<223> OTHER INFORMATION: PCR primer

<400> SEQUENCE: 45
gcagaaaggg cttagtgatg agaa                                      24

<210> SEQ ID NO 46
<211> LENGTH: 25
<212> TYPE: DNA
<213> ORGANISM: Artificial sequence
<220> FEATURE:
<223> OTHER INFORMATION: PCR primer

<400> SEQUENCE: 46
cagatgcccc ataaagactt gttaa                                     25

<210> SEQ ID NO 47
<211> LENGTH: 27
<212> TYPE: DNA
<213> ORGANISM: Artificial sequence
<220> FEATURE:
<223> OTHER INFORMATION: PCR primer

<400> SEQUENCE: 47
gattctactc tgtgcctcct gactatg                                   27

<210> SEQ ID NO 48
<211> LENGTH: 24
<212> TYPE: DNA
<213> ORGANISM: Artificial sequence
<220> FEATURE:
<223> OTHER INFORMATION: PCR primer

<400> SEQUENCE: 48
ggctgagtat gtggctttcc tatg                                      24

<210> SEQ ID NO 49
<211> LENGTH: 23
<212> TYPE: DNA
<213> ORGANISM: Artificial sequence
<220> FEATURE:
<223> OTHER INFORMATION: PCR primer

<400> SEQUENCE: 49
tgcatcagta ccccattcta tca                                       23

<210> SEQ ID NO 50
<211> LENGTH: 20
<212> TYPE: DNA
<213> ORGANISM: Artificial sequence
<220> FEATURE:
<223> OTHER INFORMATION: PCR primer

<400> SEQUENCE: 50

```
ggccttgacc ttttcagcaa                                                20

<210> SEQ ID NO 51
<211> LENGTH: 23
<212> TYPE: DNA
<213> ORGANISM: Artificial sequence
<220> FEATURE:
<223> OTHER INFORMATION: PCR primer

<400> SEQUENCE: 51
tagccttgtc agataaggaa gga                                            23

<210> SEQ ID NO 52
<211> LENGTH: 22
<212> TYPE: DNA
<213> ORGANISM: Artificial sequence
<220> FEATURE:
<223> OTHER INFORMATION: PCR primer

<400> SEQUENCE: 52
acagcttcac agtcaacttt gt                                             22

<210> SEQ ID NO 53
<211> LENGTH: 19
<212> TYPE: DNA
<213> ORGANISM: Artificial sequence
<220> FEATURE:
<223> OTHER INFORMATION: PCR primer

<400> SEQUENCE: 53
ctgggctaca ctgagcacc                                                 19

<210> SEQ ID NO 54
<211> LENGTH: 21
<212> TYPE: DNA
<213> ORGANISM: Artificial sequence
<220> FEATURE:
<223> OTHER INFORMATION: PCR primer

<400> SEQUENCE: 54
aagtggtcgt tgagggcaat g                                              21
```